(12) United States Patent
Miller et al.

(10) Patent No.: US 11,406,445 B2
(45) Date of Patent: Aug. 9, 2022

(54) ELECTROSURGICAL DEVICE

(71) Applicant: Buffalo Filter LLC, Lancaster, NY (US)

(72) Inventors: Michael J. Miller, Depew, NY (US); Samantha Bonano, Williamsville, NY (US)

(73) Assignee: Buffalo Filter LLC, Lancaster, NY (US)

( * ) Notice: Subject to any disclaimer, the term of this patent is extended or adjusted under 35 U.S.C. 154(b) by 627 days.

(21) Appl. No.: 15/669,267

(22) Filed: Aug. 4, 2017

(65) Prior Publication Data

US 2018/0036068 A1   Feb. 8, 2018

Related U.S. Application Data

(60) Provisional application No. 62/370,995, filed on Aug. 4, 2016.

(51) Int. Cl.
*A61B 18/14* (2006.01)
*A61M 1/00* (2006.01)
*A61B 18/00* (2006.01)

(52) U.S. Cl.
CPC ...... *A61B 18/1482* (2013.01); *A61B 18/1402* (2013.01); *A61M 1/741* (2021.05); *A61B 18/1442* (2013.01); *A61B 18/1492* (2013.01); *A61B 2018/0072* (2013.01); *A61B 2018/0091* (2013.01); *A61B 2018/00571* (2013.01); *A61B 2018/00916* (2013.01); *A61B 2218/007* (2013.01)

(58) Field of Classification Search
CPC ............ A61B 18/1485; A61B 18/1402; A61B 2018/00964; A61B 2218/008
See application file for complete search history.

(56) References Cited

U.S. PATENT DOCUMENTS

| | | | |
|---|---|---|---|
| 2001/0051804 A1 | 12/2001 | Mulier et al. | |
| 2002/0115917 A1* | 8/2002 | Honda | A61B 17/00 600/301 |
| 2005/0107782 A1* | 5/2005 | Reschke | A61B 18/1402 606/42 |

(Continued)

OTHER PUBLICATIONS

ISA/US, International Search Report and Written Opinion from PCT/US2017/045645, dated Oct. 18, 2017.

*Primary Examiner* — Tigist S Demie
(74) *Attorney, Agent, or Firm* — Timothy W. Menasco, Esq.; Harter Secrest & Emery LLP

(57) ABSTRACT

Presented are an apparatus, method and electrosurgical device for surgical procedures. An exemplary apparatus includes a body comprising a longitudinal axis and an electrical wire maintained within the body extending along the longitudinal axis, and an electrode extending from a distal end of the body operably coupled to the electrical wire, the electrode with the electrical wire operable to conduct a flow of current at a plurality of levels. The apparatus further includes a first button arranged on an external surface of the body, the first button operable for selecting the flow of current at each one of the plurality of levels through the electrical wire and the electrode, and a second button arranged on the external surface of the body adjacent the first button, the second button operable activate and deactivate the flow of current to the electrode.

19 Claims, 5 Drawing Sheets

(56) References Cited

U.S. PATENT DOCUMENTS

| | | | |
|---|---|---|---|
| 2007/0135812 A1* | 6/2007 | Sartor | A61B 18/1482 606/42 |
| 2009/0062786 A1* | 5/2009 | Garito | A61B 18/12 606/37 |
| 2011/0190768 A1 | 8/2011 | Shvetsov et al. | |
| 2012/0310229 A1* | 12/2012 | Gregg | A61B 17/320092 606/33 |
| 2014/0081086 A1* | 3/2014 | Shvetsov | A61B 18/1402 600/249 |
| 2015/0209100 A1* | 7/2015 | Ineson | A61B 18/1402 606/42 |
| 2015/0306348 A1 | 10/2015 | Wallace et al. | |
| 2016/0175033 A1 | 6/2016 | Le | |

\* cited by examiner

502: (a) providing a body comprising a longitudinal axis and an electrical wire maintained within the body extending along the longitudinal axis; (b) providing an electrode extending from a distal end of the body operably coupled to the electrical wire, the electrode with the electrical wire operable to conduct a flow of current at a plurality of levels; (c) providing a first button arranged on an external surface of the body, the first button operable for selecting the flow of current at each one of the plurality of levels through the electrical wire and the electrode; and (d) providing a second button arranged on the external surface of the body adjacent the first button, the second button operable activate and deactivate the flow of current to the electrode.

504: wherein the body comprises a vacuum tube defining a passageway through the longitudinal axis, the body having an inlet to the vacuum tube at the distal end of the body and an outlet to the vacuum tube at a proximal end of the body.

506: wherein the electrode comprises a metal rod or strip and is at least one of monopolar, bipolar, and sesquipolar.

508: wherein the first button is operable to at least one of slide, rock, or push.

510: wherein the plurality of levels comprises at least a cut level and a coagulate level.

512: wherein the body further comprises a hollow tube extending from the distal end of the body circumscribing the electrode.

514: wherein the first button comprises at least one of a color indicator, a word, and a light operable to indicate which one of the plurality of levels is selected by the first button.

FIG. 5

ELECTROSURGICAL DEVICE

BACKGROUND OF THE INVENTION

Field of the Invention

The present invention relates generally to the field of electrosurgical devices, and more particularly to an electrosurgical device operable to cut and coagulate and a method of using such a system.

Description of Related Art

Surgical smoke and aerosol, or plume, is created in connection with surgery. For example, when laser or electrosurgical energy is delivered to a cell, heat is created. This heat vaporizes the intracellular fluid, which increases the pressure inside the cell and eventually causes the cell membrane to burst. In this example, a plume of smoke containing water vapor is released into the atmosphere of the operating room or doctor's office. At the same time, the heat created may char the protein and other organic matter within the cell, and may cause thermal necrosis in adjacent cells. The charring of cells may also release other harmful contaminants, such as carbonized cell fragments and gaseous hydrocarbons.

BRIEF SUMMARY OF THE INVENTION

In view of the foregoing, it is an object of the present disclosure to provide a method and apparatus for surgical procedures.

A first exemplary embodiment of the present disclosure provides an apparatus for surgical procedures. The apparatus includes a body comprising a longitudinal axis and an electrical wire maintained within the body extending along the longitudinal axis, and an electrode extending from a distal end of the body operably coupled to the electrical wire, the electrode with the electrical wire operable to conduct a flow of current at a plurality of levels. The apparatus further includes a first button arranged on an external surface of the body, the first button operable for selecting the flow of current at each one of the plurality of levels through the electrical wire and the electrode, and a second button arranged on the external surface of the body adjacent the first button, the second button operable activate and deactivate the flow of current to the electrode.

A second exemplary embodiment of the present disclosure provides a method. The method includes providing a body comprising a longitudinal axis and an electrical wire maintained within the body extending along the longitudinal axis, and providing an electrode extending from a distal end of the body operably coupled to the electrical wire, the electrode with the electrical wire operable to conduct a flow of current at a plurality of levels. The method further includes providing a first button arranged on an external surface of the body, the first button operable for selecting the flow of current at each one of the plurality of levels through the electrical wire and the electrode, and providing a second button arranged on the external surface of the body adjacent the first button, the second button operable activate and deactivate the flow of current to the electrode.

A third exemplary embodiment of the present disclosure provides an electrosurgical device for surgical procedures. The electrosurgical device includes a tubular body comprising a longitudinal axis and an electrical rod extending from a distal end of the longitudinal axis, the electrical rod operably connected to an electrical wire maintained within the tubular body, the tubular body comprising a hollow air path extending through the longitudinal axis. The electrosurgical device further includes a first button located on an external surface of the tubular body operable for selecting a flow of current to the electrical rod at a plurality of levels, and a second button located on the external surface of the body adjacent the first button, the second button operable activate and deactivate the flow of current to the electrical rod.

The following will describe embodiments of the present invention, but it should be appreciated that the present disclosure is not limited to the described embodiments and various modifications of the invention are possible without departing from the basic principles. The scope of the present disclosure is therefore to be determined solely by the appended claims.

BRIEF DESCRIPTION OF THE SEVERAL VIEWS OF THE DRAWING(S)

FIG. 5 is a logic flow diagram in accordance with a method and apparatus for performing exemplary embodiments of this disclosure.

DETAILED DESCRIPTION OF THE INVENTION

Figure 1:
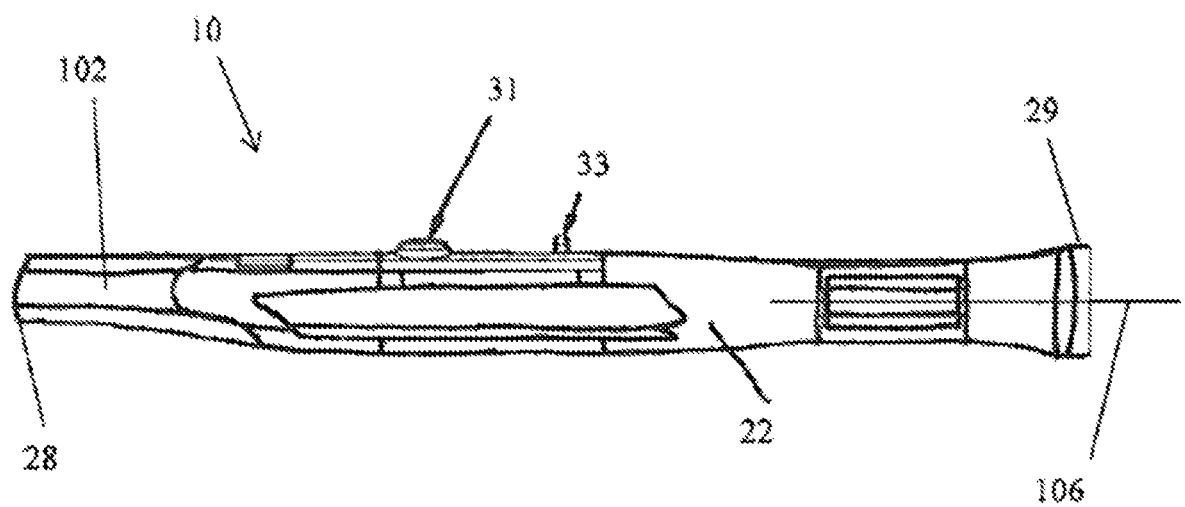
FIG. 1 is a side view of an exemplary electrosurgical device suitable for use in practicing exemplary embodiments of this disclosure.
Figure 2:
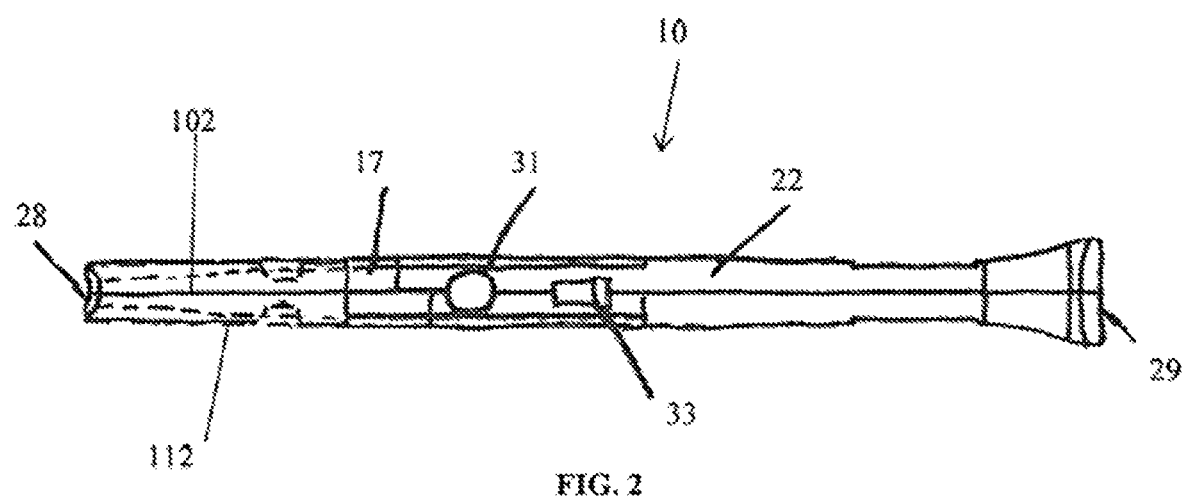
FIG. 2 is a top view of an exemplary electrosurgical device suitable for use in practicing exemplary embodiments of this disclosure.
Figure 3:
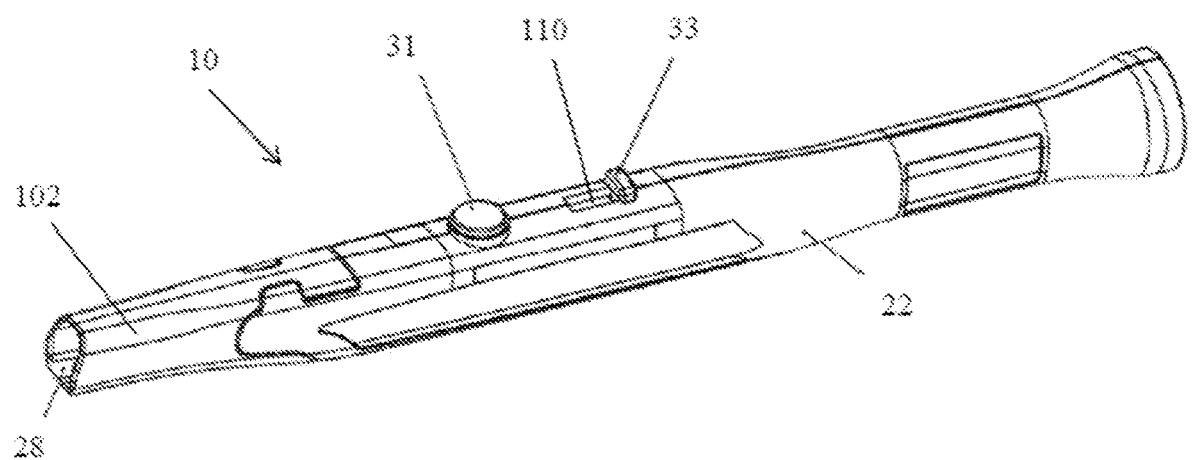
FIG. 3 is a perspective view of an exemplary electrosurgical device suitable for use in practicing exemplary embodiments of this disclosure.

At the outset, it should be clearly understood that like reference numerals are intended to identify the same structural elements, portions or surfaces consistently throughout the several drawing figures, as such elements, portions or surfaces may be further described or explained by the entire written specification, of which this detailed description is an integral part. Unless otherwise indicated, the drawings are intended to be read (e.g., cross-hatching, arrangement of parts, proportion, debris, etc.) together with the specification, and are to be considered a portion of the entire written description of this invention. As used in the following description, the terms "horizontal", "vertical", "left", "right", "up" and "down", as well as adjectival and adverbial derivatives thereof, (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or of rotation, as appropriate.

Referring to FIGS. 1-4, merely for the purposes of illustration and not by way of limitation, the present embodiment provides an electrosurgical device 10 having an elongated body 22 having a longitudinal axis identified by line 106. Body 22 also includes a passageway 26, a distal end 28, a proximal end 29, and an external surface 17.

Figure 4:
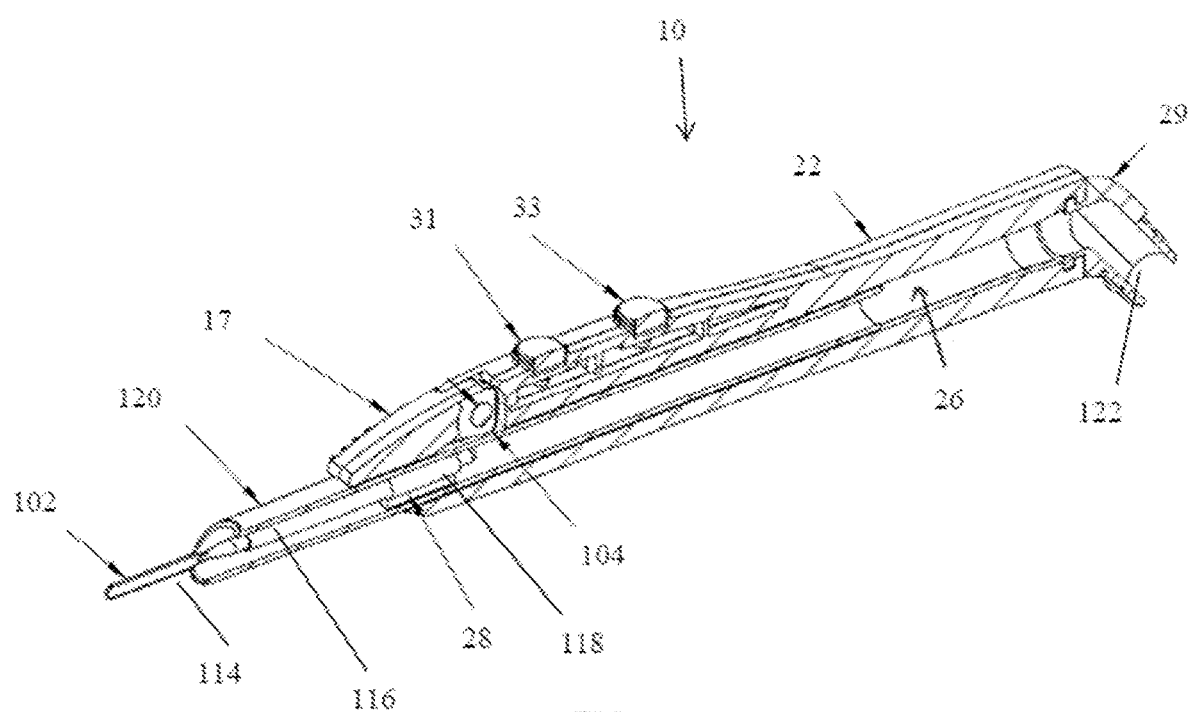
FIG. 4 is a cross-sectional perspective view of an exemplary electrosurgical device suitable for use in practicing exemplary embodiments of this disclosure.

Shown in FIG. 4 is an electrode 102 disposed at the distal end 28. Electrode 102 is operably coupled to an electrical wire 104 arranged within the body 22. Electrode 102 and electrical wire 104 are operable to conduct a flow of current at a plurality of levels or a plurality of power levels. The body 22 may be configured to reversibly receive a portion of electrode 102 at the distal end 28 of the body 22 such that electrical contact is made between the electrode 102 and the electrical wire 104. The electrode 102 may have an uninsulated distal portion 114, an insulated portion 116 and a mounting portion 118 that engages with body 22 and electrical wire 104. The insulated portion 31 may be provided in applications where the user may have a need to remove the electrode 102 and replace it with a different electrode 102.

A first button 33 is arranged on an external surface 17 of body 22. First button 33 is operable for selecting the flow of current at each one of the plurality of levels through the electrical wire and the electrode. In other words, first button 33 located on body 22 provides for changing between multiple levels of current. Embodiments of first button 33 include a button that is operable to slide, rock, or be pushed relative to body 22. Embodiments of first button 33 are operable for changing between a flow of current that allows electrode 102 to be used as a cut function and a coagulate function. The cut function operates at a higher level of current than a coagulate function as will be evident to persons of ordinary skill in the art. Embodiments of first button 33 include an audio indicator 108 or a visual indicator 110 operable to show the user which function has been selected. Embodiments of visual indicator 110 are operable to visually indicate which one of the plurality of levels are selected by first button 33. Embodiments of visual indicator 110 are operable to provide a color-changing button, a window, lights, words or any other means to provide feedback to the user.

Body 22 also includes a second button 31 located on the external surface 17 operable for activating or deactivating a flow of current through electrical wire 104 and electrode 102 at a power level selected by first button 33. In other words, second button 31 is operable to allow a flow of current at multiple levels such as at a first level, a second level and/or a wave pattern.

Body 22 also includes a hollow tube 112 extending from the distal end 28 of the body 22. Embodiments of hollow tube 112 circumscribe the electrode 102. Embodiments of hollow tube 112 can be clear or opaque, and can be removeably attached to body 22.

The body 22 may be ergonomically shaped to be received by a user's hand. In one embodiment, body 22 is shaped as a pencil. Embodiments of electrode 102 include an electrode that is monopolar, bipolar, or sesquipolar.

As will be evident to those of ordinary skill in the art based on this disclosure, the first button 33 controls the level of current through electric wire 104 inside the electrosurgical device 10. Electric wire 104 is electrically connected to an electrode 102 which is used for electrocautery procedures. First button 33 provides for use of a single ergonomically placed second button 31 that can be used for both the cut and coagulate functions.

Embodiments of electrosurgical device 10 include a passageway 26 (shown in FIG. 4) extending through the longitudinal axis 106 of body 22. Body 22 includes an inlet 120 fluidly connected by passageway 26 to an outlet 122. Inlet 120, passageway 26 and outlet 122 are operable to allow a flow of gas, air or surgical smoke to pass through inlet 120, passageway 26 and outlet 122.

FIG. 5 presents a summary of the above teachings for aiding in surgical procedures. Block 502 presents (a) providing a body comprising a longitudinal axis and an electrical wire maintained within the body extending along the longitudinal axis; (b) providing an electrode extending from a distal end of the body operably coupled to the electrical wire, the electrode with the electrical wire operable to conduct a flow of current at a plurality of levels; (c) providing a first button arranged on an external surface of the body, the first button operable for selecting the flow of current at each one of the plurality of levels through the electrical wire and the electrode; and (d) providing a second button arranged on the external surface of the body adjacent the first button, the second button operable activate and deactivate the flow of current to the electrode. Then block 504 specifies wherein the body comprises a vacuum tube defining a passageway through the longitudinal axis, the body having an inlet to the vacuum tube at the distal end of the body and an outlet to the vacuum tube at a proximal end of the body.

Some of the non-limiting implementations detailed above are also summarized at FIG. 5 following block 504. Block 506 relates to wherein the electrode comprises a metal rod or strip and is at least one of monopolar, bipolar, and sesquipolar. Block 508 states wherein the first button is operable to at least one of slide, rock, or push. Block 510 details wherein the plurality of levels comprises at least a cut level and a coagulate level. Next block 512 states wherein the body further comprises a hollow tube extending from the distal end of the body circumscribing the electrode. Finally block 514 relates to wherein the first button comprises at least one of a color indicator, a word, and a light operable to indicate which one of the plurality of levels is selected by the first button. The logic flow diagram of FIG. 5 may be considered to illustrate the operation of a method or the result of a method of providing.

The present invention contemplates that many changes and modifications may be made. Therefore, while the presently-preferred form of the electrosurgical device has been shown and described, and several modifications and alternatives discussed, persons skilled in this art will readily appreciate that various additional changes and modifications may be made without departing from the spirit of the invention, as defined and differentiated by the following claims.

The invention claimed is:

1. An apparatus for surgical procedures, the apparatus comprising:
   a body comprising a longitudinal axis, the body defining a hollow tube having a passageway, a fluid inlet at a distal end, and a fluid outlet at a proximal end, the body maintains an electrical wire within the body extending along the longitudinal axis, wherein the fluid inlet and the fluid outlet are fluidly connected by the passageway;
   an electrode circumscribed by the hollow tube extending from the distal end of the body operably coupled to the electrical wire, the electrode comprising an uninsulated distal portion, an insulated portion and a mounting portion for coupling with the body and the electrical wire, the electrode with the electrical wire operable to conduct a flow of current at a plurality of levels;
   a first button arranged on an external surface of the body, the first button operable for selecting a level of the flow of current through the electrical wire and the electrode from the plurality of levels, wherein the first button comprises a light operable to indicate which one of the plurality of levels is selected by the first button; and
   a second button arranged on the external surface of the body adjacent the first button, the second button operable to activate and deactivate the flow of current to the electrode at the level selected by the first button from the plurality of levels.

2. The apparatus according to claim 1, wherein the body comprises a vacuum tube defining a passageway through the longitudinal axis, the body having an inlet to the vacuum tube at the distal end of the body and an outlet to the vacuum tube at a proximal end of the body.

3. The apparatus according to claim 1, wherein the electrode comprises a metal rod or strip and is at least one of monopolar, bipolar, and sesquipolar.

4. The apparatus according to claim 1, wherein the first button is operable to at least one of slide, rock, or push.

5. The apparatus according to claim 1, wherein the plurality of levels comprises at least a cut level and a coagulate level.

6. The apparatus according to claim 1, the apparatus further comprising an audio indicator operable to transmit an audio alert based on which one of the plurality of levels is selected by the first button.

7. The apparatus according to claim 1, wherein the first button comprises at least one of a color indicator, or a word operable to indicate which one of the plurality of levels is selected by the first button.

8. A method comprising:
(a) providing a body comprising a longitudinal axis and an electrical wire maintained within the body extending along the longitudinal axis, the body defining a hollow tube having a passageway, a fluid inlet at a distal end, and a fluid outlet at a proximal end, wherein the fluid inlet and the fluid outlet are fluidly connected by the passageway;
(b) providing an electrode extending from the distal end of the body operably coupled to the electrical wire, the electrode with the electrical wire operable to conduct a flow of current at a plurality of levels, the electrode comprising an uninsulated distal portion, an insulated portion and a mounting portion for coupling with the body and the electrical wire;
(c) providing a first button arranged on an external surface of the body, the first button operable for selecting a level of the flow of current through the electrical wire and the electrode from the plurality of levels, wherein the first button comprises a light operable to indicate which one of the plurality of levels is selected by the first button; and
(d) providing a second button arranged on the external surface of the body adjacent the first button, the second button operable to activate and deactivate the flow of current to the electrode at the level selected by the first button from the plurality of levels.

9. The method according to claim 8, wherein the body comprises a vacuum tube defining a passageway through the longitudinal axis, the body having an inlet to the vacuum tube at the distal end of the body and an outlet to the vacuum tube at a proximal end of the body.

10. The method according to claim 8, wherein the electrode comprises a metal rod or strip and is at least one of monopolar, bipolar, and sesquipolar.

11. The method according to claim 8, wherein the first button is operable to at least one of slide, rock, or push.

12. The method according to claim 8, wherein the plurality of levels comprises at least a cut level and a coagulate level.

13. The method according to claim 8, wherein the hollow tube extends from the distal end of the body circumscribing the electrode.

14. The method according to claim 8, wherein the first button comprises at least one of a color indicator, or a word operable to indicate which one of the plurality of levels is selected by the first button.

15. An electrosurgical device for surgical procedures, the electrosurgical device comprising:
a tubular body comprising a longitudinal axis and an electrical rod extending from a distal end of the longitudinal axis, the tubular body having a hollow air path, a fluid inlet at the distal end, and a fluid outlet at a proximal end, wherein the fluid inlet and the fluid outlet are fluidly connected by the hollow air path, the electrical rod operably connected to an electrical wire maintained within the tubular body, the hollow air path extending through the longitudinal axis;
a first button located on an external surface of the tubular body operable for selecting a level of flow of current to the electrical rod at a plurality of levels, wherein the first button comprises a light operable to indicate which one of the plurality of levels is selected by the first button; and
a second button located on the external surface of the body adjacent the first button, the second button operable to activate and deactivate the flow of current to the electrical rod at the level selected by the first button from the plurality of levels.

16. The electrosurgical device according to claim 15, wherein the plurality of levels comprises at least a cut level and a coagulate level.

17. The electrosurgical device according to claim 15, the electrosurgical device further comprising an evacuation tube fluidly coupled to the hollow air path, and a vacuum, and wherein the electrosurgical device is operable to evacuate surgical smoke from a surgical site through the hollow air path and the evacuation tube.

18. The electrosurgical device according to claim 15, wherein the first button is operable to at least one of slide, rock, or push.

19. The electrosurgical device according to claim 15, wherein the first button comprises at least one of a color indicator, or a word operable to indicate which one of the plurality of levels is selected by the first button.

* * * * *